United States Patent [19]
Wheeler

[11] Patent Number: 5,380,268
[45] Date of Patent: Jan. 10, 1995

[54] BODY FLUID FLOW CONTROL VALVE AND METHOD

[76] Inventor: Douglas E. Wheeler, 1715 Enclave Pkwy., #307, Houston, Tex. 77077

[21] Appl. No.: 72,082

[22] Filed: Jun. 7, 1993

[51] Int. Cl.⁶ .............................................. A61F 2/02
[52] U.S. Cl. ......................... 600/30; 128/DIG. 25
[58] Field of Search ........................ 600/29–31; 604/320, 321; 128/DIG. 25; 251/65 (U.S. only)

[56] References Cited

U.S. PATENT DOCUMENTS

| | | | |
|---|---|---|---|
| 5,004,454 | 4/1991 | Beyar et al. | 128/DIG. 25 |
| 5,041,092 | 8/1991 | Barwick | 600/29 |

FOREIGN PATENT DOCUMENTS 1194358  6/1970  United Kingdom ............... 600/30

Primary Examiner—J. L. Kruter
Attorney, Agent, or Firm—William W. Haefliger

[57] ABSTRACT

A method and device for controlling urine flow from the bladder in a body which includes providing a magnetically responsive valve of a size to fit in the urethra, and providing a valve actuating magnet; installing the valve in the urethra, in the path of urine flow; and operating the valve between urine flow passing and urine flow blocking states, by controlling the position of the actuating magnet, outside the body, whereby the magnetic field of the actuating magnet effects the operating of the valve.

11 Claims, 3 Drawing Sheets

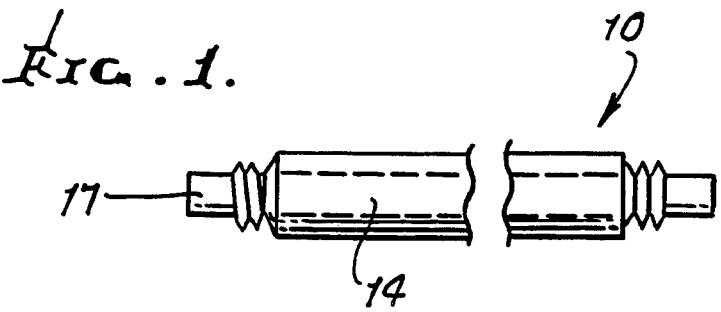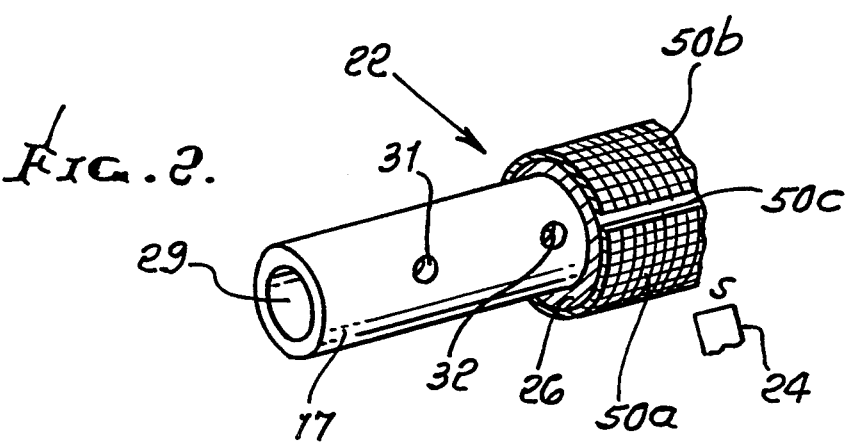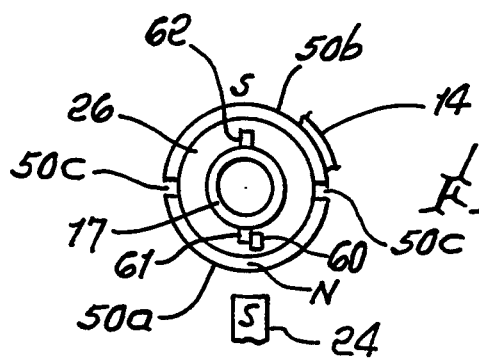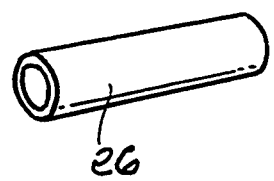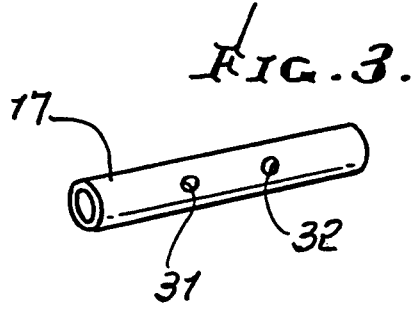

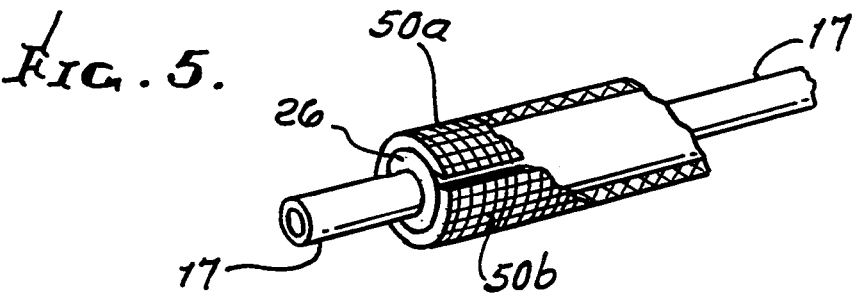
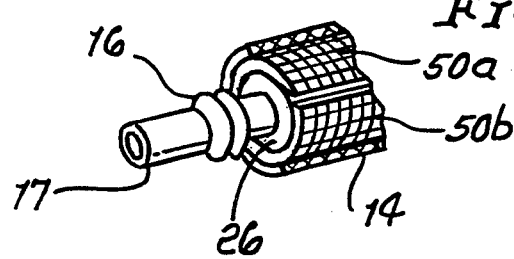
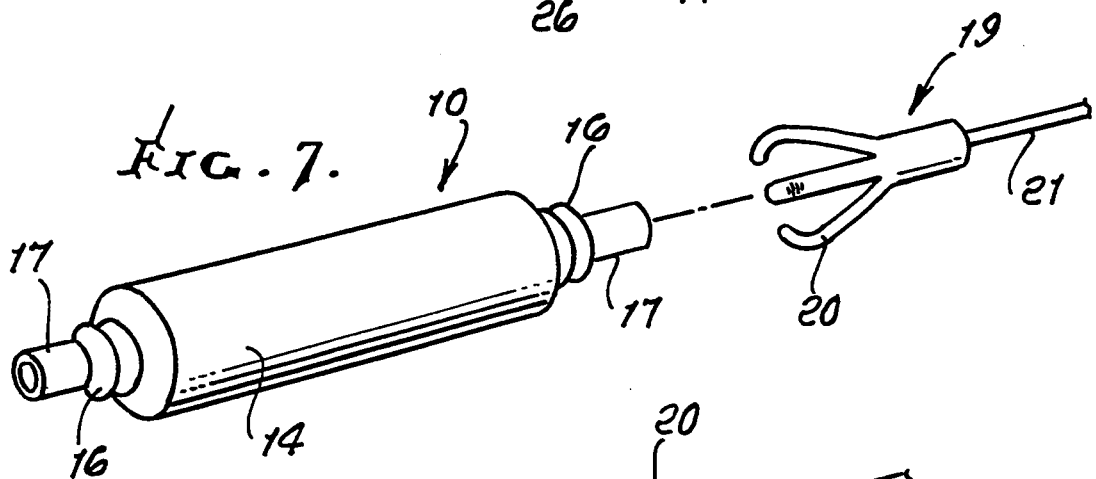
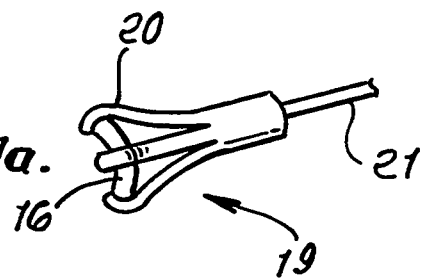
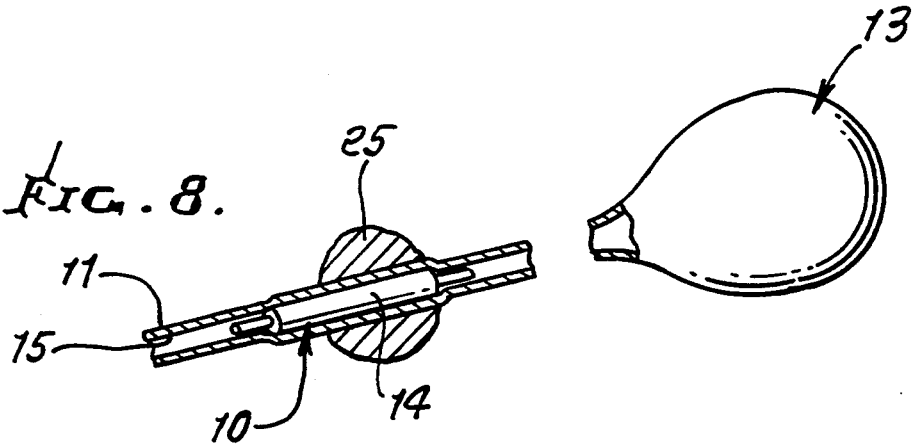

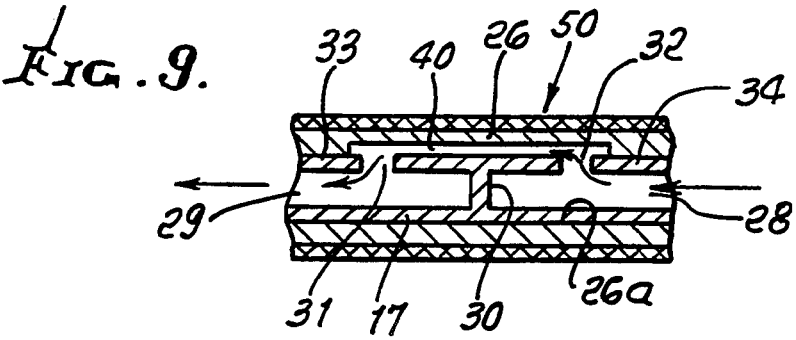
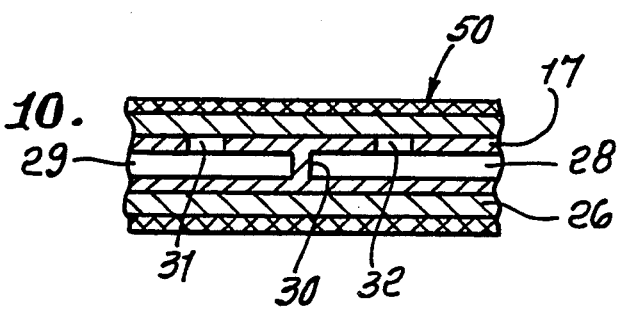
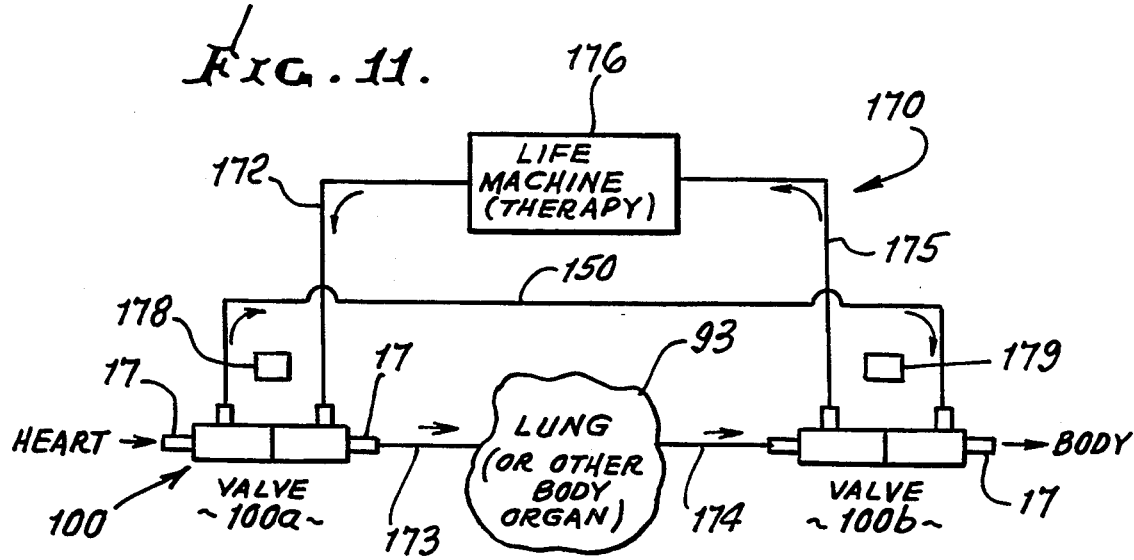
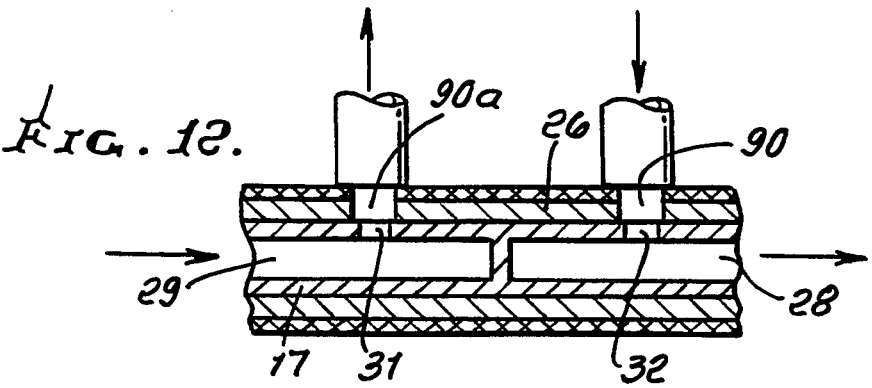

BODY FLUID FLOW CONTROL VALVE AND METHOD

BACKGROUND OF THE INVENTION

This invention relates generally to control of body fluid flow by external means, obviating need for elongated catheters in the body; more particularly it concerns provision and usage of a novel valving apparatus inserted in a body flow duct, and externally operable as by a magnetic field or fields.

There is critical need for means that enables external control of body fluid flow, in the body (as for example urine or blood), without requiring elongated catheter placement in the body, thereby alleviating suffering. There is also need for means other than the use of diapers, to deal with and remedy incontinence problems. Other similar needs exist, without the effective solutions as are now afforded by the present invention.

SUMMARY OF THE INVENTION

It is a major object of the invention to provide method and means to meet and resolve the above needs in a simple, effective manner.

In the case of control of urine flow from the bladder, the method of the invention includes the steps:

a) providing a magnetically responsive valve of a size to fit in the urethra, and providing a valve actuating magnet, b) installing the valve in the urethra, in the path of urine flow, c) and operating the valve between urine flow passing and urine flow blocking states, by controlling the position of the actuating magnet, outside the body, whereby the magnetic field of the actuating magnet effects said operating of the valve.

Typically, the valve is provided to have a rotary valving element, with magnetic pole means thereon providing a magnetic field, and the operation of the valve by controlling the position of the actuating magnet is effected by causing the magnetic field of the actuating magnet to interact with the magnetic field of the rotary valving element pole means, for rotating the valving element.

As will be seen, the valving element is typically provided to have OPEN and CLOSED positions between which the valving element is movable, and said controlling of the position of the actuating magnet is effected to first move the valving element to OPEN POSITION, in which urine flows in the urethra from the bladder, and thereafter to move the valving element to CLOSED position, in which urine flow in the urethra is blocked by the valving element.

Considering the external control of body fluids generally, in a body internal duct, the method includes the steps:

a) providing a magnetically responsive valve of a size to be inserted in series with said duct, and providing a valve actuating magnet, b) the valve provided to have a rotary valving element, with magnetic pole means thereon providing a magnetic field, c) inserting the valve in said body passage, in the path of body fluid flow, d) and effecting rotation of the valving element between body fluid flow passing and flow blocking positions, by controlling the position of said actuating magnet, outside the body, thereby causing the magnetic field of the actuating magnet to interact with the magnetic field of the rotary valving element pole means.

It is a further object of the invention to provide apparatus meeting the above needs, such apparatus comprising:

a) a magnetically responsive valve of a size to be inserted in series with said internal duct, to be responsive to a separate valve actuating magnet, b) the valve having a body structure and a rotary valving element rotatable relative to said structure, the said element having magnetic pole means providing a magnetic field, c) the valving element being rotatable between body fluid flow passing and flow blocking positions, by controlling the position outside the body of said actuating magnets, thereby causing the magnetic field of the actuating magnet to interact with the magnetic field of the rotary valving element pole means.

Another object is to provide magnetically responsive valves in a body organ isolating liquid flow circuit or circuits.

These and other objects and advantages of the invention, as well as the details of an illustrative embodiment, will be more fully understood from the following specification and drawings, in which:

DRAWING DESCRIPTION

FIG. 1 is a side view of valve apparatus incorporating the invention;

FIG. 2 is a perspective view, broken away, showing details of the FIG. 1 apparatus;

FIG. 2a is an end view of valving elements;

FIG. 3 is a perspective view of a continual non-rotary tube incorporated in FIGS. 1 and 2;

FIG. 4 is a perspective view of a rotary valving element sleeve, rotatable about the FIG. 3 tube;

FIG. 5 is a perspective view of magnet cylinder assembled on the FIG. 4 sleeve to rotate therewith;

FIG. 6 is a view like FIG. 5 showing a housing about the magnet cylinder;

FIG. 7 is a view like FIG. 6, showing the complete apparatus, with an inserting tool;

FIG. 7a is a view showing use of the tool;

FIG. 8 shows the FIG. 7 apparatus inserted in a body duct, such as the urethra;

FIG. 9 is an enlarged fragmentary section, showing the rotary sleeve rotated about the core structures, into a flow OPEN position;

FIG. 10 is a view like FIG. 9 showing the rotary sleeve rotated about the core structures into a flow CLOSED position;

FIG. 11 shows an alternative apparatus in a dual flow enabling position; and

FIG. 12 shows a valve configuration as used in FIG. 11.

DETAILED DESCRIPTION

In the drawings, apparatus 10 is provided to be inserted or implanted in a body fluid flow duct 11, internally in the body (such as a human body). Such a duct may comprise the urethra (see FIG. 8) to pass urine from bladder 13, or it may comprise a blood vessel such as an artery, or it may comprise some other duct such as a semen flow duct.

The apparatus typically includes an elongated cylindrical housing 14 sized to be slightly larger in diameter than the internal diameter 15 of the duct 11, for retention in that duct at a selected location. FIG. 7 shows the apparatus as having annular grips or flanges 16 at and integral with opposite ends of the housing, and extending about a smaller diameter tubular core 17. An insertion tool 19 has grip engaging fingers 20 that can grip the flange or flanges 16 at one end of the apparatus, for inserting the latter endwise into selected position in duct 11. Fingers 20 are operated (opened or closed) as via an endoscopic flexible shaft 21, manipulable to insert the apparatus. FIG. 7a shows closing of the fingers on a flange 16.

The apparatus 10 is shown in FIG. 2, for example to include a magnetically responsive valve 22 within housing 14 (better seen in FIG. 6) to be responsive to a separate and external valve actuating magnet, as indicated at 24, outside the human or animal body 25. Valve 22 includes a movable (rotary) element such as sleeve 26, and the non-rotary core 17, on which the sleeve 26 rotates. Core 17 and housing 14 are non-rotatable, and may be gripped by vessel 11. Core 17 may be cylindrical as shown, and have two bore sections 28 and 29 separated by a wall 30, as seen in FIG. 9. Bore section 28 communicates with duct 11 in one direction, and bore section 29 communicates with duct 11 in the opposite direction. Ports 31 and 32 are formed in the side walls 33 and 34 of the bore sections, at opposite sides of wall 30. Sleeve 26 has a bore 26a closely slidable on the cylindrical outer surface of the core, to provide a sealing effect. The sleeve has a longitudinally elongated port 40 formed along and outwardly of bore 26a, to register with ports 31 and 32 when the sleeve is in a first (OPEN) rotary position, thereby to pass fluid endwise through the apparatus 10. See FIG. 9. Alternatively, the port 40 is out of registration with ports 31 and 32 when the sleeve is in a second (CLOSED) rotary position, whereby fluid is then prevented from passing through the apparatus. See FIG. 10. The two (first and second) positions may correspond to sleeve rotary positions 180° apart, about the axis of the core.

A magnetic means 50 extends at least part way about, and on, the sleeve 26. Thus, a NORTH pole magnet section 50a may extend slightly less than 180° above the sleeve, and a SOUTH pole magnet section 50b may extend slightly less than 180° about the sleeve, the sections 50a and 50b being disjunct. See gaps 50c in FIGS. 2 and 2a. Sections 50a and 50b rotate with the sleeve. Tubular housing 14 then extends sealingly about sections 50a and 50b (see FIG. 6). External magnet 24 is externally manually manipulated to cause its north or south pole alternately to be directed toward the apparatus 10 in the duct 11, to cause its magnetic field to interact with the fields of the sections 50a and 50b, to effect rotation of the rotor to valve OPEN, or CLOSED position as desired (i.e. to enable or block drainage of urine from the bladder). Suitable stops are provided on 26 and 17 (or 14) to limit rotation of 26 in valve OPEN or CLOSED position. FIG. 2a schematically shows arm 60 on the sleeve 26 that engages stop arm 61 on the core 17 in one retaining position, and engages stop arm 62 on the core in the other rotary position of the sleeve. These are representative only.

FIG. 11 shows a modified device 100 comprising two three-way type valves 100a and 100b connected as shown. These are like valve 22, except that a third through port 90 in sleeve 26 registers with passage 28 via port 32 when the core 17 rotates to a position as seen in FIG. 12; and a third port 90a in sleeve 26 registers with passage 29, via port 31 at that time. Looking at valve 100a, in one rotary position of its sleeve 26, blood flows endwise through the valve as in FIG. 9, as to lung 93, then to and endwise through like valve 100b as in normal blood flow to the lung. Valves 100a and 100b are inserted in blood vessels leading to and from the lungs. In the alternate positions of sleeves 26 in both valves, blood flows radially out from port 90 in the sleeve 26 in valve 100a, then through an external duct 150 to the port 90a sleeve 26 of the other valve 100b, and then endwise from the core 17 to resume flow in the patient's circulatory system. External duct 150 bypasses the lung, which may then be isolated as for surgery. A lung monitoring system 170 may then be simultaneously connected with the lung, as shown, to supply blood or other fluid to the lung via isolated circuit that includes duct 172, port 90 and passage 28 in valve 100a, blood vessel 173, lung 93, blood vessel 174, passage 28 and port 90 in valve 100b, and duct 175 back to machine 176, which may include a blood pump. Valve actuating magnets appear at 178 and 179.

In the above, the cores 17 and sleeves 26 may consist of ceramic material. Where magnetic fields are referred to, they may be magnetic or electric; and where magnets are referred to, they may be permanent or electromagnetic, or electric.

I claim:

1. The method of controlling urine flow from the bladder in a body which includes the steps:
   a) providing an axially endwise elongated magnetically responsive cylindrical valve of a size to fit in the urethra, providing grip means at an end of the valve, and providing a valve actuating magnet,
   b) installing the valve in the urethra, by providing a tool having grip finger means and operating the tool to cause said finger means to grip said grip means for advancing the valve endwise in the urethra, in the path of urine flow,
   c) and operating the valve between urine flow passing and urine flow blocking states, by controlling the position of the actuating magnet, outside the body, whereby the magnetic field of the actuating magnet effects said operating of the valve.

2. The method of claim 1 wherein said valve is provided to have a rotary valving element, with magnetic pole means thereon providing a magnetic field, and said operating of the valve by controlling said position of the actuating magnet is effected by causing the magnetic field of the actuating magnet to interact with the magnetic field of the rotary valving element pole means, for rotating said valving element.

3. The method of claim 1 wherein said valving element is provided to have OPEN and CLOSED positions between which the valving element is movable, and said controlling of the position of the actuating magnet is effected to first move the valving element to OPEN position, in which urine flows in the urethra from the bladder, and thereafter to move the valving element to CLOSED position, in which urine flow in the urethra is blocked by the valving element.

4. The method of claim 1 wherein said valve means includes a first element which is rotatable and a second element which is non-rotatable, the rotatable element carrying magnetic structure, said elements having flow ports, and said method including magnetically rotating the rotatable element to bring said flow ports into and out of flow passing communication to effect said operating of the valve means between flow passing and flow blocking states, and operating said finger means to grip said grip means, endwise of the valve.

5. The method of controlling body fluid flow in a body internal duct, which includes the steps:
   a) providing an axially endwise elongated magnetically responsive cylindrical valve of a size to be inserted in series with said duct, and providing a valve actuating magnet,
   b) said valve provided to have a rotary valving element, with magnetic pole means thereon providing a magnetic field,
   c) inserting said valve in said duct, by providing a tool having grip finger means and operating the tool to cause said finger means to grid said grip means for advancing the valve endwise in the urethra, in the duct,
   d) and effecting rotation of the valving element between body fluid flow passing and flow blocking positions, by controlling the position of said actuating magnet, outside the body, thereby causing the magnetic field of the actuating magnet to interact with the magnetic field of the rotary valving element pole means.

6. The method of claim 5 wherein said body fluid consists of one of the following:
   i) urine
   ii) blood
   iii) semen.

7. In apparatus for controlling urine flow from a bladder in a body, the combination comprising
   a) an endwise elongated magnetically responsive valve of a size to fit in series with the urethra in the body and to be responsive to a separate valve actuating magnet,
   b) the valve having a movable valving element with magnetic pole means providing a magnetic field,
   c) the valving element being movable between urine flow passing and urine flow blocking states, by controlling the position of the actuating magnet causing the magnetic field of the movable valving element pole means,
   d) there being grip means on the valve at one end thereof, the valve having a cylindrical outer surface, the grip means located within a cylinder defined by said surface, to be gripped by gripping tool finger means to advance the valve in the urethra.

8. The combination of claim 7 wherein said valving element is a rotor, and said valve includes structures extending within said rotor and enabling said rotor to rotate between OPEN position in which urine flows in the urethra from the bladder, and CLOSED position in which urine flow in the urethra is blocked.

9. The combination of claim 8 wherein said rotor defines first and third flow ports, and said structure defines a second flow port, said ports being in flow passing series communication in said OPEN position, and said second port rotated out of flow passing series communication with said first and third ports in said CLOSED position, said grip means defining flange means extending about one of said flow ports at the end of the valve and spaced from said end.

10. In apparatus for controlling body fluid flow in a body internal duct, the combination comprising:
    a) an endwise elongated magnetically responsive valve of a size to be inserted in series with said internal duct, to be responsive to a separate valve actuating magnet,
    b) the valve having a body structure and a rotary valving element rotatable relative to said structure, the said element having magnetic pole means providing a magnetic field,
    c) the valving element being rotatable between body fluid flow passing and flow blocking positions, by controlling the position outside the body of said actuating magnet, thereby causing the magnetic field of the actuating magnet to interact with the magnetic field of the rotary valving element pole means,
    d) there being grip means on the valve at one end thereof, the valve having a cylindrical outer surface, the grip means located within a cylinder defined by said surface, to be gripped by gripping tool finger means to advance the valve in the urethra, in said duct.

11. The combination of claim 10 wherein said valve receives said body fluid which consists of one of the following:
    i) urine
    ii) blood
    iii) semen.

* * * * *